(12) United States Patent
Schlotterback et al.

(10) Patent No.: US 9,662,103 B2
(45) Date of Patent: May 30, 2017

(54) SYSTEMS AND METHODS FOR BONE ANCHOR INSERTER DEPTH INDICATION

(75) Inventors: Ryan Schlotterback, Fort Wayne, IN (US); Justin C. Anderson, Minnetonka, MN (US)

(73) Assignee: Tornier, Inc., Bloomington, MN (US)

( * ) Notice: Subject to any disclaimer, the term of this patent is extended or adjusted under 35 U.S.C. 154(b) by 718 days.

(21) Appl. No.: 13/240,857

(22) Filed: Sep. 22, 2011

(65) Prior Publication Data

US 2012/0245633 A1    Sep. 27, 2012

Related U.S. Application Data

(60) Provisional application No. 61/385,801, filed on Sep. 23, 2010.

(51) Int. Cl.
| | | |
|---|---|---|
| *A61B 17/58* | (2006.01) | |
| *A61B 17/60* | (2006.01) | |
| *A61F 2/00* | (2006.01) | |
| *A61B 17/04* | (2006.01) | |
| *A61B 90/00* | (2016.01) | |

(52) U.S. Cl.
CPC .. *A61B 17/0401* (2013.01); *A61B 2017/0409* (2013.01); *A61B 2090/062* (2016.02)

(58) Field of Classification Search
CPC .............. A61B 19/46; A61B 2019/461; A61B 2019/462
USPC .................. 606/232, 95–99, 104, 86 A, 102
See application file for complete search history.

(56) References Cited

U.S. PATENT DOCUMENTS

| | | |
|---|---|---|
| 4,994,074 A | 2/1991 | Bezwada et al. |
| 5,258,016 A | 11/1993 | DiPoto et al. |
| 5,405,359 A | 4/1995 | Pierce |
| 5,540,718 A | 7/1996 | Bartlett |
| 5,683,418 A | 11/1997 | Luscombe et al. |
| 5,782,863 A | 7/1998 | Bartlett |
| 5,792,143 A | 8/1998 | Samuelson et al. |

(Continued)

FOREIGN PATENT DOCUMENTS

| | | |
|---|---|---|
| EP | 1 611 852 | 1/2006 |
| GB | 2452825 A | 3/2009 |

(Continued)

OTHER PUBLICATIONS

Extended European Search Report issued in European Application No. 11182211.0, dated Jul. 29, 2013, in 6 pages.

(Continued)

*Primary Examiner* — Ellen C Hammond
*Assistant Examiner* — Christina Negrellirodrigue
(74) *Attorney, Agent, or Firm* — Knobbe, Martens, Olson & Bear, LLP

(57) ABSTRACT

A bone anchor inserter according to embodiments of the present invention includes a shaft configured to interface with a bone anchor, a proper depth indicator on the shaft, an upper visual indicator on the shaft, the upper visual indicator located adjacent to the proper depth indicator on a first side of the proper depth indicator furthest from the bone anchor, and a lower visual indicator on the shaft, the lower visual indicator located adjacent to the proper depth indicator on a second side of the proper depth indicator opposite from the first side, the lower visual indicator being visually distinct from the upper visual indicator.

13 Claims, 3 Drawing Sheets

(56) References Cited

U.S. PATENT DOCUMENTS

| | | |
|---|---|---|
| 5,961,538 A | 10/1999 | Pedlick et al. |
| 5,993,458 A * | 11/1999 | Vaitekunas ........ A61B 17/0401 |
| | | 606/104 |
| 5,993,477 A | 11/1999 | Vaitekunas et al. |
| 6,045,571 A | 4/2000 | Hill et al. |
| 6,264,674 B1 | 7/2001 | Washington et al. |
| 6,270,518 B1 | 8/2001 | Pedlick et al. |
| 6,306,158 B1 | 10/2001 | Bartlett |
| 6,890,308 B2 | 5/2005 | Islam |
| 7,938,847 B2 | 5/2011 | Fanton et al. |
| 8,029,536 B2 | 10/2011 | Sorensen et al. |
| 2005/0288682 A1* | 12/2005 | Howe ................ A61B 17/0401 |
| | | 606/104 |
| 2006/0178702 A1 | 8/2006 | Pierce et al. |
| 2007/0112384 A1 | 5/2007 | Conlon et al. |
| 2007/0167950 A1* | 7/2007 | Tauro ................ A61B 17/0401 |
| | | 606/326 |
| 2007/0225719 A1 | 9/2007 | Stone et al. |
| 2007/0260259 A1 | 11/2007 | Fanton et al. |
| 2008/0275469 A1 | 11/2008 | Fanton et al. |
| 2009/0069823 A1 | 3/2009 | Foerster et al. |
| 2009/0082786 A1 | 3/2009 | Surti |
| 2009/0149960 A1 | 6/2009 | Hushka et al. |
| 2009/0312793 A1 | 12/2009 | Huxel et al. |
| 2011/0046632 A1* | 2/2011 | Quevedo ........................ 606/102 |
| 2012/0010471 A1* | 1/2012 | Mire ...................... A61M 29/00 |
| | | 600/210 |
| 2012/0245631 A1 | 9/2012 | Lunn et al. |
| 2013/0110165 A1 | 5/2013 | Burkhart et al. |
| 2013/0197577 A1 | 8/2013 | Wolf et al. |
| 2013/0197578 A1 | 8/2013 | Gregoire et al. |
| 2013/0197579 A1 | 8/2013 | Foerster et al. |

FOREIGN PATENT DOCUMENTS

| | | |
|---|---|---|
| WO | 2005065597 A2 | 7/2005 |
| WO | 2007117366 A2 | 10/2007 |
| WO | 2010036864 A9 | 4/2010 |

OTHER PUBLICATIONS

DePuy Mitek, Inc., "MicroFix Absorbable QuickAnchor Plus", 2005.

DePuy Mitek, Inc., "MiniLok Absorbable QuickAnchor Plus", 2005.

DePuy Mitek, Inc., PanaLok RC QuickAnchor Plus Absorbable Anchor, 2006.

* cited by examiner

SYSTEMS AND METHODS FOR BONE ANCHOR INSERTER DEPTH INDICATION

CROSS-REFERENCE TO RELATED APPLICATION

This application claims the benefit of U.S. Provisional Patent Application Ser. No. 61/385,801, filed on Sep. 23, 2010, which is incorporated by reference herein in its entirety for all purposes.

TECHNICAL FIELD

Embodiments of the present invention relate generally to visual depth indication for bone anchor insertion.

BACKGROUND

When a surgeon inserts a bone anchor through tissue (e.g. a tendon) and into bone, it is often difficult for the surgeon to determine how deeply the anchor is being inserted with the insertion tool. If the bone anchor inserter is inserted to an incorrect depth, later challenges may be exacerbated, for example with bone anchors or suture anchors which must then be deployed or fastened after placement.

SUMMARY

A bone anchor inserter according to embodiments of the present invention includes markings and/or etchings oriented longitudinally along the shaft above the bone anchor portion. The markings and/or etchings include an indication located longitudinally along the inserter shaft corresponding to a proper or desired insertion depth; for example, the inserter shaft includes a circumferential and/or horizontal and/or lateral line or other mark at the desired proper depth location (which may be referred to as a proper depth indicator), an upper visual indicator longitudinally above the mark, and lower visual indicator longitudinally below the mark that is different and distinct from the upper visual indicator. In this way, a surgeon lifting the tissue through which the inserter and anchor have been inserted can perform a visual inspection of the inserter between the top (outer) bone surface and the bottom (underside) tissue surface to determine whether the inserter needs to be inserted deeper (when the surgeon sees only the lower visual indication), whether the inserter is just in between the proper depth and a depth just above the proper depth (when the surgeon sees the proper depth indicator as well as the upper and lower visual indicators), or whether the inserter is inserted to the proper depth (when the surgeon sees only the upper visual indicator).

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
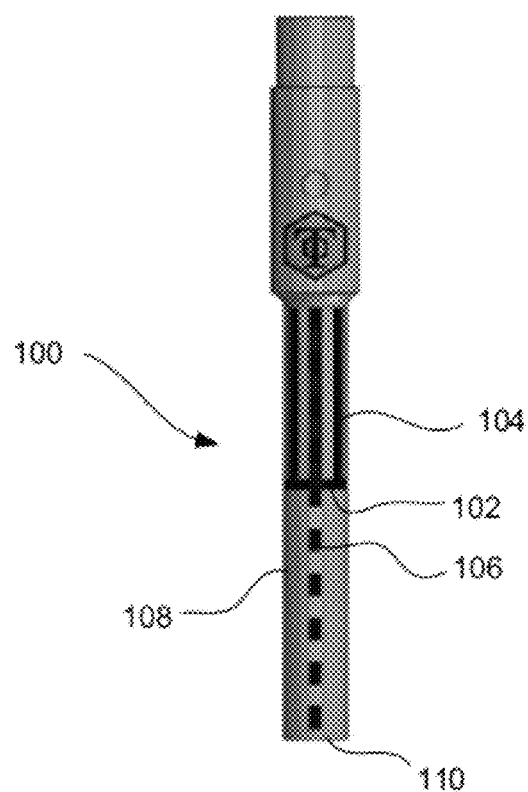
FIG. 1 illustrates a partial front elevation view of a bone anchor inserter with visual indicators, according to embodiments of the present invention.
Figure 2:
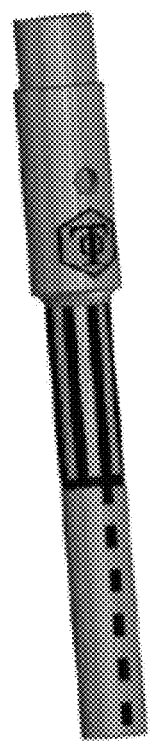
FIG. 2 illustrates a partial front perspective view of the bone anchor inserter of FIG. 1.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A bone anchor inserter 100 according to embodiments of the present invention includes markings and/or etchings 102, 104, 106 oriented longitudinally along the shaft 108 above the end 110 of the shaft 108 which includes or interfaces with or is coupled to the bone anchor 200 portion. The markings and/or etchings include an indication 102 located longitudinally along the inserter shaft corresponding to a proper or desired insertion depth; for example, the inserter shaft includes a circumferential and/or horizontal and/or lateral line or other mark 102 at the desired proper depth location (which may be referred to as a proper depth indicator 102), an upper visual indicator 104 longitudinally above the mark 102, and lower visual indicator 106 longitudinally below the mark 102 that is different and distinct from the upper visual indicator. The upper visual indicator 104 as depicted is a set of longitudinally-extending solid lines spaced radially about an axial centerline of the shaft 108. The upper visual indicator 104 is in visual communication with, that is to say abuts or extends directly from or in contact with, the proper depth indicator 102, according to embodiments of the present invention. The lower visual indicator 106 as depicted is one or more longitudinally-extending dashed lines. The lower visual indicator 106 is also in visual communication with, or abuts or extends directly from or in contact with, the proper depth indicator 102, according to embodiments of the present invention. The upper visual indicator 104 is visually distinct from the lower visual indicator 106, such that a surgeon observing only a small longitudinal extent of either indicator 104, 106 can determine which indicator 104, 106 is being observed. The circumferential nature of the proper depth indicator 102 also visually sets it apart from both the upper visual indicator 104 and the lower visual indicator 106. According to some embodiments of the present invention, the upper visual indicator 104, lower visual indicator 106, and/or proper depth indicator 102 are laser etched into the shaft 108.

In this way, a surgeon lifting the tissue through which the inserter and anchor have been inserted can perform a visual inspection of the inserter between the top (outer) bone surface and the bottom (underside) tissue surface to determine whether the inserter 100 needs to be inserted deeper (when the surgeon sees only the lower visual indicator 106), whether the inserter 100 is just in between the proper depth and a depth just above the proper depth (when the surgeon sees the proper depth indicator 102 as well as the upper and lower visual indicators 104, 106), or whether the inserter 100 is inserted to the proper depth (when the surgeon sees only the upper visual indicator 104). For example, using the example shown in FIG. 1, if the surgeon glances under the tissue and sees only one dashed line (which may indicate suture orientation as well), the surgeon knows that the anchor and anchor inserter must go deeper. If the surgeon sees only vertical lines all around, the surgeon knows that the proper depth has been reached. If the surgeon sees both vertical lines and a dashed line, and/or the proper depth indicator 102, the surgeon will know to go deeper.

Figure 6:
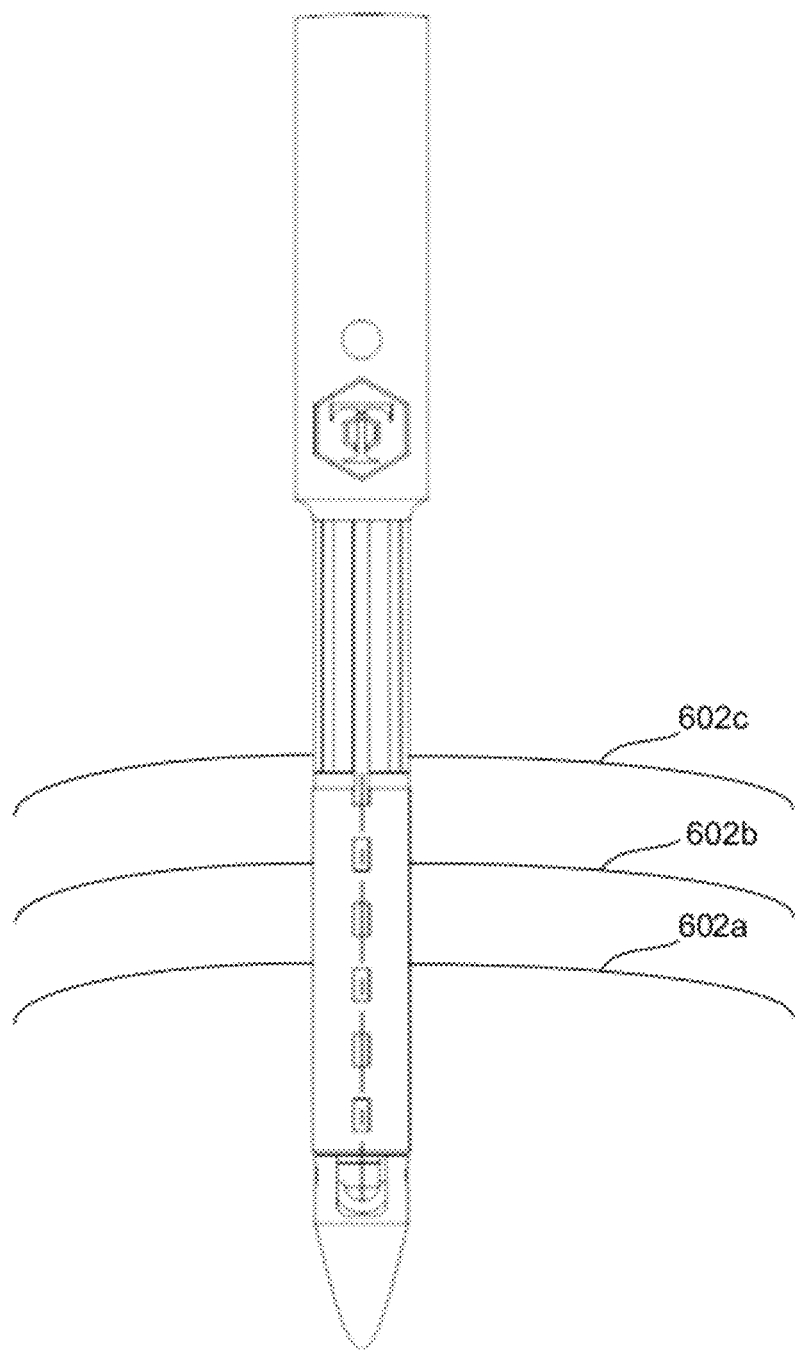
FIG. 6 illustrates the enlarged front elevation view of the bone anchor inserter of FIG. 4 in different positions with respect to an outer surface of bone, according to embodiments of the present invention.

FIG. 6 illustrates this concept. The top of the bone surface is illustrated in various positions 602a, 602b, 602c with respect to the inserter 100, according to embodiments of the present invention. When the surgeon sees the top of the bone surface in position 602a, the surgeon knows that the anchor and anchor inserter must go deeper. When the surgeon sees the top of the bone surface in position 602b, the surgeon likewise knows that the anchor and anchor inserter must go deeper. When the surgeon sees the top of the bone surface in position 602c, the surgeon knows that the proper depth has been reached, according to embodiments of the present invention.

According to some embodiments, one or more of the upper or lower visual indicators 104, 106 may indicate suture orientation. For example, the anchor inserter 100 and the bone anchor used therewith may be one or more of the anchor inserters and suture anchors described in U.S. Patent Application Publication No. 2007/0260259, published Nov. 8, 2007, which is incorporated by reference herein in its entirety for all purposes. As one example, the lower visual indicator 106 may be a single dashed line which is aligned with the suture which has been threaded through an anchoring and/or locking and/or suture retention mechanism within the suture anchor and/or bone anchor, thereby permitting the surgeon to twist the bone anchor inserter about its longitudinal axis to achieve desired suture alignment. Such positioning of the bone anchor insertion tool 300 may be facilitated by handle 302, according to embodiments of the present invention.

Figure 5:
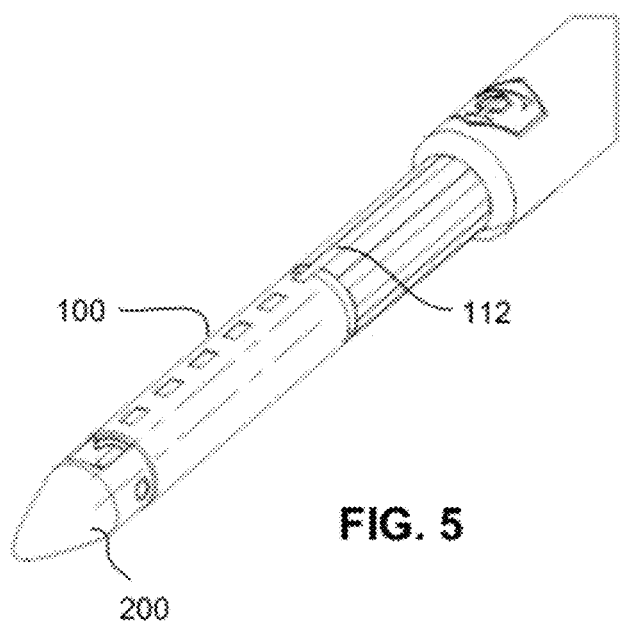
FIG. 5 illustrates a front perspective view of the bone anchor inserter and bone anchor of FIGS. 3 and 4, according to embodiments of the present invention.
Figure 3:
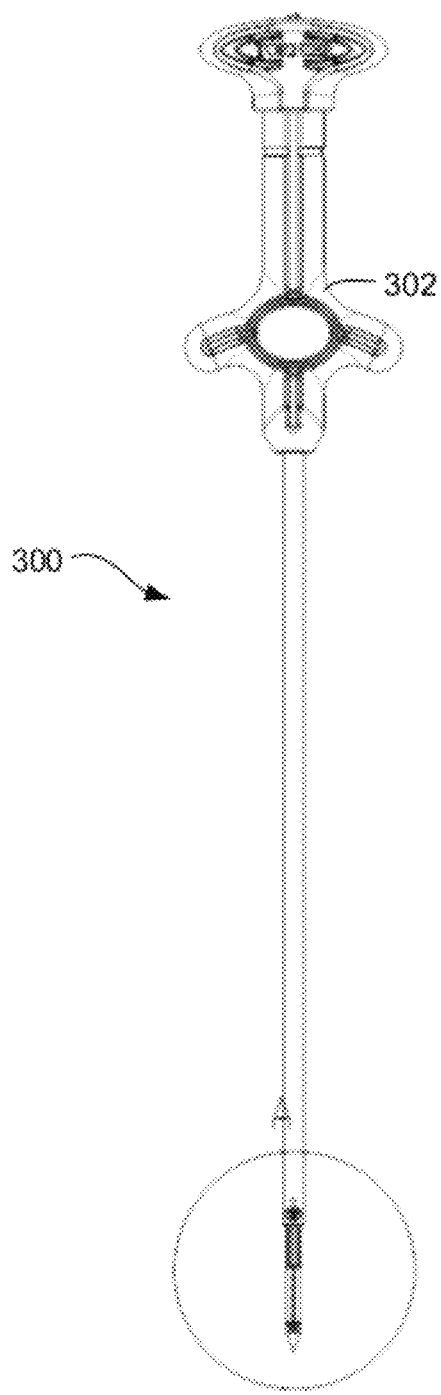
FIG. 3 illustrates a front elevation view of a bone anchor insertion tool with bone anchor inserter and bone anchor, according to embodiments of the present invention.
Figure 4:
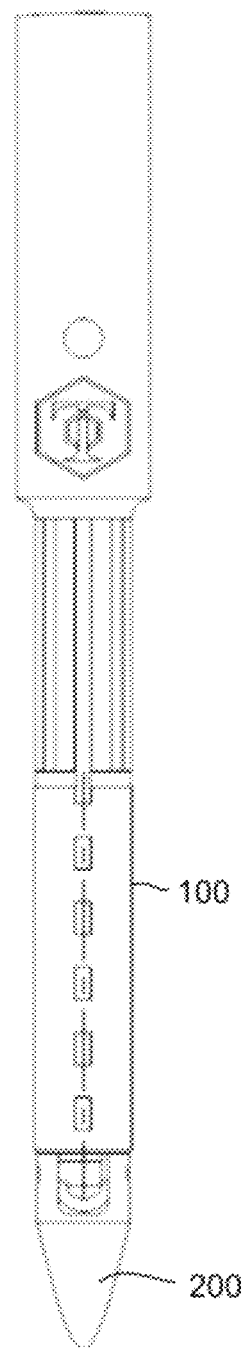
FIG. 4 illustrates an enlarged front elevation view of the bone anchor inserter and bone anchor of FIG. 3 taken within circle A of FIG. 3, according to embodiments of the present invention.

According to some embodiments of the present invention, the lower visual indicator 106 may include a dashed line on each side of the shaft 108, such that the rear elevation view of the shaft 108 is the same as the front elevation view of the shaft 108 shown in FIGS. 1 and 4, according to embodiments of the present invention. The upper visual indicator 104 may further include an indication of suture alignment, for example, one of the longitudinally-extending vertical lines 112, and/or one of such lines 112 on each side of the shaft 108, may be visually distinct from the other longitudinally-extending lines. For example, line 112 may be a different color or thickness or pattern than the other radially-spaced, longitudinally-extending lines in the upper visual indicator 104. As shown in FIGS. 4 and 5, a suture threaded through the bone anchor 200 may include one strand which extends along the dashed line of lower visual indicator 106 and another strand which extends along the other dashed line (separated radially from the first dashed line by 180 degrees) on the other side of the lower visual indicator 106. In this way, a surgeon can determine suture orientation in addition to depth information. The anchor 200 may be coupled to the shaft 108 in such a way so as to restrict rotation of the anchor 200 with respect to the longitudinal axis, such that the suture orientation indicators are accurate, according to embodiments of the present invention.

According to some embodiments of the present invention, the anchor 200 is of a type which permits suture to be tightened by pulling on one of two strands in order to tighten the other of the two strands. The upper and/or lower visual indicators 104, 106 may further be configured to indicate which of the two suture strands corresponds to the strand to be attached to the tissue, and/or which of the two suture strands corresponds to the strand to be pulled for tightening, according to embodiments of the present invention.

Although particular patterns are shown for upper and lower visual indicators 104, 106 and for proper depth indicator 102, one of ordinary skill in the art, based on the present disclosure, will appreciate that numerous other indicators may be used, including but not limited to line patterns, colors, longitudinally diverging or converging shapes or lines or sets thereof, etchings, engravings, printings, stickers, or any other elements capable of indicating a visual distinction. For example, a solid color may be applied above the proper depth indicator 102, and a different solid color or a lack of color may be applied below the proper depth indicator 102, according to embodiments of the present invention. According to some embodiments of the present invention, the proper depth indicator 102 is not a separate visual feature, but is merely the interface between the upper and lower visual indicators 104, 106. For example, the proper depth indication of FIG. 1 may be the longitudinal location along the shaft 108 at which the upper visual indicator 104 meets the lower visual indicator 106, according to embodiments of the present invention.

The visual indicator system may be used for visualizing under the cuff in a transtendon repair, according to embodiments of the present invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A system for bone anchor insertion, the system comprising:
   a bone anchor;
   a shaft configured to interface with the bone anchor;
   a suture engaged with the bone anchor and extending within the shaft;
   a proper depth indicator on the shaft, the proper depth indicator extending entirely around the perimeter of the shaft;
   an upper visual indicator on the shaft, the upper visual indicator located adjacent to the proper depth indicator on a first side of the proper depth indicator furthest from the bone anchor; and
   a lower visual indicator on the shaft, the lower visual indicator located adjacent to the proper depth indicator on a second side of the proper depth indicator opposite from the first side, the lower visual indicator being visually distinct from the upper visual indicator.

2. The system of claim 1, wherein the proper depth indicator is an interface between the upper visual indicator and the lower visual indicator.

3. The system of claim 1, wherein the proper depth indicator is a line formed at a particular longitudinal distance from the bone anchor.

4. The system of claim 1, wherein one of the upper and lower visual indicators comprises a solid line, and wherein the other of the upper and lower visual indicators comprises a dashed line.

5. The system of claim 1, wherein the upper visual indicator comprises a set of longitudinally-extending solid lines spaced radially about an axial centerline of the shaft.

6. The system of claim 5, wherein the lower visual indicator comprises at least one longitudinally-extending dashed line.

7. The system of claim 1, wherein the upper visual indicator comprises a first color, and wherein the lower visual indicator comprises a second color that is visually distinct from the first color.

8. The system of claim 1, wherein at least one of the upper visual indicator and the lower visual indicator visually indicates an orientation of the suture within the shaft.

9. The system of claim 8, wherein both of the upper visual indicator and the lower visual indicator visually indicate the orientation of the suture within the shaft.

10. The system of claim 8, further comprising a handle adapted to permit twisting of the shaft about a longitudinal axis of the shaft to achieve alignment between the suture and the at least one of the upper visual indicator and the lower visual indicator indicating the orientation of the suture.

11. The system of claim 1, wherein the suture comprises a first strand and a second strand extending within the shaft, and wherein at least one of the upper visual indicator and the lower visual indicator visually indicates an orientation of both the first strand and the second strand.

12. The system of claim 11, wherein both of the upper visual indicator and the lower visual indicator visually indicate the orientation of both the first strand and the second strand.

13. The system of claim 1, wherein the upper visual indicator comprises a set of longitudinally-extending solid lines spaced radially about an axial centerline of the shaft, and wherein at least one of the set of longitudinally-extending solid lines is visually distinct from the other solid lines of the set and visually indicates an orientation of the suture within the shaft.

* * * * *